United States Patent
He et al.

(10) Patent No.: US 10,800,734 B2
(45) Date of Patent: Oct. 13, 2020

(54) MEMANTINE COMPOUNDS AND THEIR PREPARATION AND USES THEREOF

(71) Applicant: Sunshine Lake Pharma Co., Ltd., Dongguan, Guangdong (CN)

(72) Inventors: Bifei He, Guangdong (CN); Yuping Fan, Guangdong (CN); Huixiong Lu, Guangdong (CN); Guangyuan Liu, Guangdong (CN); Zhongqing Wang, Guangdong (CN); Zhonghua Luo, Guangdong (CN)

(73) Assignee: Sunshine Lake Pharma Co., Ltd., Dongguan, Guangdong (CN)

( * ) Notice: Subject to any disclaimer, the term of this patent is extended or adjusted under 35 U.S.C. 154(b) by 0 days.

(21) Appl. No.: 16/094,848

(22) PCT Filed: May 5, 2017

(86) PCT No.: PCT/CN2017/083129
§ 371 (c)(1),
(2) Date: Oct. 18, 2018

(87) PCT Pub. No.: WO2017/193870
PCT Pub. Date: Nov. 16, 2017

(65) Prior Publication Data
US 2019/0144378 A1 May 16, 2019

(30) Foreign Application Priority Data
May 7, 2016 (CN) .......................... 2016 1 0300245

(51) Int. Cl.
| | | |
|---|---|---|
| C07C 271/24 | (2006.01) | |
| A61K 31/27 | (2006.01) | |
| A61K 31/445 | (2006.01) | |
| A61K 31/473 | (2006.01) | |
| A61K 31/4748 | (2006.01) | |
| A61K 31/55 | (2006.01) | |
| A61K 31/225 | (2006.01) | |
| A61K 45/06 | (2006.01) | |
| A61K 31/235 | (2006.01) | |
| C07C 269/06 | (2006.01) | |
| C07C 269/02 | (2006.01) | |
| C07C 269/04 | (2006.01) | |
| A61P 3/10 | (2006.01) | |
| A61P 25/28 | (2006.01) | |

(52) U.S. Cl.
CPC .......... *C07C 271/24* (2013.01); *A61K 31/225* (2013.01); *A61K 31/235* (2013.01); *A61K 31/27* (2013.01); *A61K 31/445* (2013.01); *A61K 31/473* (2013.01); *A61K 31/4748* (2013.01); *A61K 31/55* (2013.01); *A61K 45/06* (2013.01); *A61P 25/28* (2018.01); *C07C 269/02* (2013.01); *C07C 269/04* (2013.01); *C07C 269/06* (2013.01); *C07C 2603/74* (2017.05)

(58) Field of Classification Search
CPC .......................... C07C 271/24; C07C 2603/74
See application file for complete search history.

(56) References Cited

U.S. PATENT DOCUMENTS

| | | |
|---|---|---|
| 10,441,565 B2 | 10/2019 | Sun et al. |
| 2015/0210712 A1 | 7/2015 | Blumberg et al. |

FOREIGN PATENT DOCUMENTS

| | | |
|---|---|---|
| CN | 1634859 | 7/2005 |
| CN | 103553932 | 2/2014 |
| WO | WO 01/62706 | 8/2001 |
| WO | WO-2014/134306 | 9/2014 |
| WO | WO 2017/035733 | 3/2017 |
| WO | WO-2017035733 | 3/2017 |

OTHER PUBLICATIONS

International Search Report and Written Opinion of PCT/CN2017/083129 dated Jul. 24, 2017 (12 pages).
Joubert, Jacques et al., Synthesis and evaluation of lurorescent heterocyclic aminoadamantanes as multifunctional neruoprotective agents:, Bioorg, Med. Chem. vol. 19, May 24, 2011, pp. 3935-3944.
U.S. Appl. No. 16/343,165, filed Apr. 18, 2019, Ye et al.
International Preliminary Report on Patentability for International Application No. PCT/CN2017/083129 dated Nov. 13, 2018. (8 pages).
International Preliminary Report on Patentability for International Application No. PCT/CN2017/109055 dated May 7, 2019. (6 pages).
International Search Report and Written Opinion for International Application No. PCT/CN2017/109055 dated Jan. 3, 2018. (9 pages).

*Primary Examiner* — Susanna Moore
(74) *Attorney, Agent, or Firm* — Sheppard Mullin Richter & Hampton LLP

(57) ABSTRACT

Provided are compounds of formula (I), or a stereoisomer, mixture of stereoisomers, deuterated analog, tautomer, solvate or pharmaceutically acceptable salt thereof, compositions, method of making and uses thereof.

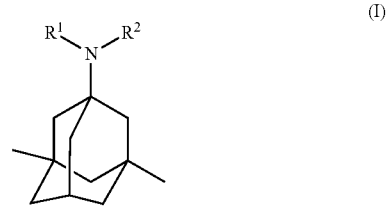

15 Claims, 1 Drawing Sheet

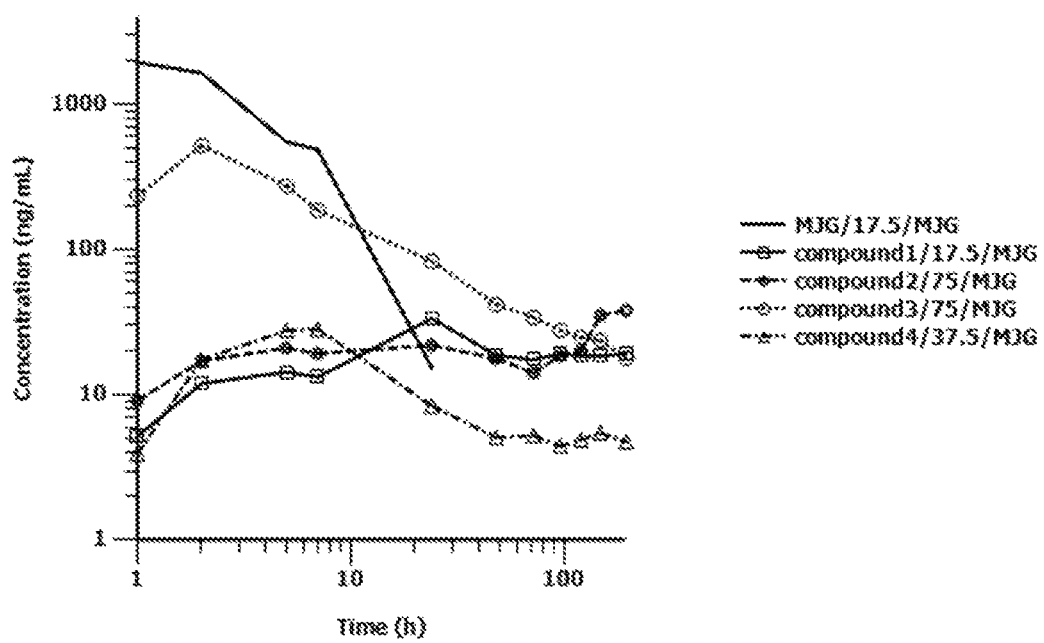

MEMANTINE COMPOUNDS AND THEIR PREPARATION AND USES THEREOF

CROSS REFERENCE TO RELATED APPLICATIONS

The present application is a national stage application of International Application PCT/CN2017/083129, filed May 5, 2017, which claim priority of Chinese Patent Application No.: 201610300245.5, filed May 7, 2016, the contents of which are incorporated by reference in their entireties into the present disclosure.

BACKGROUND

Many neurodegenerative diseases occur as a result of the neurodegenerative processes. Neurodegeneration is the progressive loss of structure or function of neurons, including death of neurons. Neurodegenerative diseases are hardly curable, resulting in progressive degeneration and/or death of neuron cells.

Memantine is an N-methyl-D-aspartate (NMDA) receptor antagonist, and it reduces certain types of brain activity by binding to NMDA receptors on brain cells and blocking the activity of the neurotransmitter glutamate. Memantine has been shown to have therapeutic effects on moderate-to-severe Alzheimer's disease and in dementia with Lewy bodies. It has also been demonstrated that memantine has efficacy in treating various diabetic diseases or conditions. The structure of memantine is shown as follows:

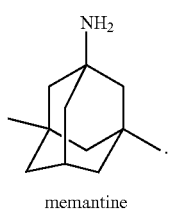

memantine

However, memantine has certain physical and chemical properties that limit its therapeutic use. For instance, memantine has fairly high water solubility which presents challenges for drug formulation. In addition, the use of memantine is associated with adverse effects such as confusion, dizziness, drowsiness, headache, insomnia, agitation, and hallucinations.

SUMMARY

This present disclosure provides memantine derivatives with reduced solubility which enables their formulation into a microcrystalline or nanocrystalline suspension. Due to the lower solubility, these derivatives can form a diffusion layer on the surface of the crystals, thus controlling the release of the drug, which can help reduce or avoid many of the adverse effects associated with memantine.

In one embodiment, this disclosure provides a compound of formula (I):

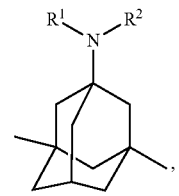

or a stereoisomer, mixture of stereoisomers, deuterated analog, tautomer, solvate or pharmaceutically acceptable salt thereof, wherein:

$R^1$ is H, an amino-protecting group, alkyl, alkenyl, alkynyl, cycloalkyl, heterocyclyl, aryl or heteroaryl;

$R^2$ is

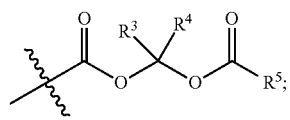

$R^3$ and $R^4$ are each independently H, alkyl, alkenyl, alkynyl, cycloalkyl or aryl; and $R^5$ is alkyl, alkenyl, alkynyl, cycloalkyl, heterocyclyl, aryl or heteroaryl, wherein each alkyl, alkenyl, alkynyl, cycloalkyl, heterocyclyl, aryl and heteroaryl of $R^1$, $R^2$, $R^3$, $R^4$, and $R^5$ are each independently optionally substituted with one or more substituents selected from halo, CN, $N_3$, $NO_2$, amino, hydroxy, mercapto, alkyl, alkylamino, dialkylamino, alkoxy, alkylacyl, alkenylacyl, alkylthio, haloalkyl, haloalkenyl, haloalkynyl, hydroxyalkyl, aminoalkyl, mercaptoalkyl, alkylaminoalkyl, dialkylaminoalkyl, alkoxyalkyl, alkylacylalkyl, alkenylacylalkyl, alkylthioalkyl, cycloalkyl, heterocyclyl, aryl and heteroaryl.

In some embodiments, $R^1$ is H, an amino-protecting group or $C_{1-6}$ alkyl optionally substituted with one or more substituents selected from halo, CN, $N_3$, $NO_2$, amino, hydroxyl, mercapto, $C_{1-6}$ alkoxy, $C_{6-10}$ aryl, $C_{2-10}$ heterocyclyl and $C_{1-9}$ heteroaryl. In some embodiments, $R^3$ and $R^4$ are each independently H or $C_{1-9}$ alkyl.

In some embodiments, $R^5$ is $C_{1-30}$ alkyl, $C_{2-30}$ alkenyl, $C_{2-30}$ alkynyl, $C_{6-14}$ aryl or $C_{1-9}$ heteroaryl, wherein the $C_{1-30}$ alkyl, $C_{2-30}$ alkenyl, $C_{2-30}$ alkynyl, $C_{6-14}$ aryl, $C_{1-9}$ heteroaryl is optionally substituted with one or more substituents selected from halo, CN, $N_3$, $NO_2$, amino, hydroxyl, mercapto, $C_{1-30}$ alkylamino, $C_{1-30}$ dialkylamino, $C_{1-30}$ alkoxy, $C_{1-30}$ alkylacyl, $C_{2-30}$ alkenylacyl, $C_{1-30}$ alkylthio, $C_{6-14}$ aryl and $C_{1-9}$ heteroaryl. In some embodiments, $R^5$ is naphthylmethyl, phenyl, benzyl, methyl, propyl, isopropyl, octyl, hendecyl, tridecyl, pentadecyl or heptadecyl.

In some embodiments, the compound is represented by formula (Ia):

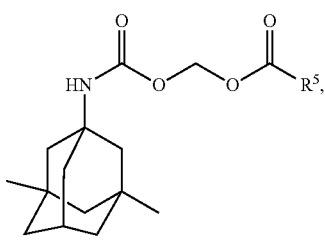

Ia or a stereoisomer, mixture of stereoisomers, deuterated analog, tautomer, solvate or pharmaceutically acceptable salt thereof, wherein $R^5$ is $C_{1-30}$ alkyl, $C_{6-10}$ aryl or $C_{1-30}$ alkyl substituted with $C_{6-10}$ aryl.

In some embodiments, provided is a compound selected from the group consisting of:

(1)

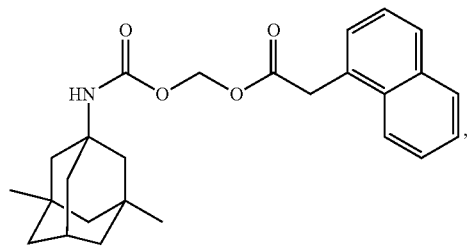

(2)

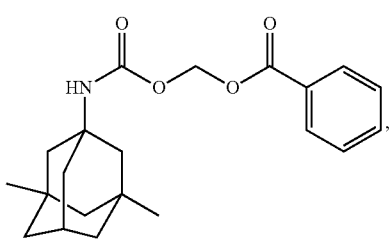

(3)

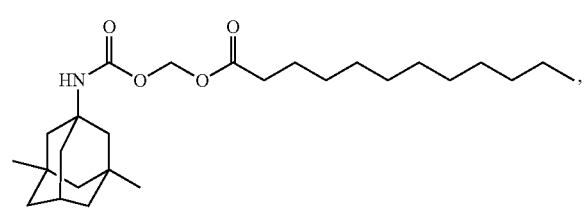

(4)

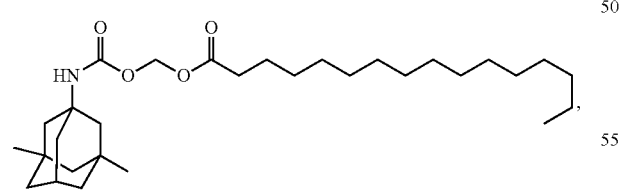

(5)

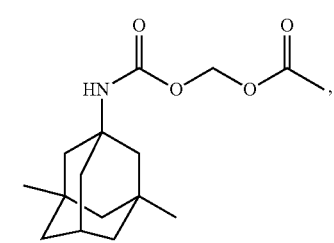

(6)

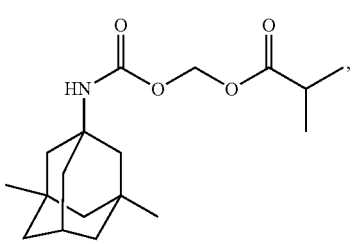

(7)

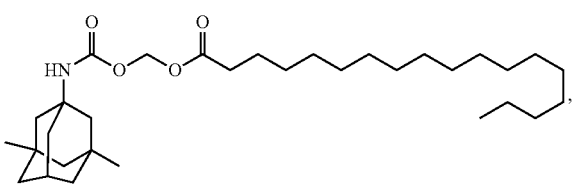

(8)

, and (9)

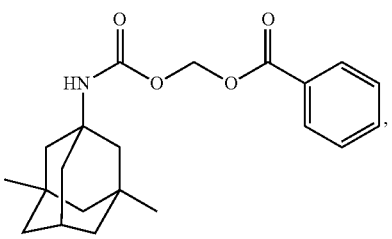

or a stereoisomer, mixture of stereoisomers, deuterated analog, tautomer, solvate or pharmaceutically acceptable salt thereof.

In a particular embodiment, the compound is (2)

or a stereoisomer, mixture of stereoisomers, deuterated analog, tautomer, solvate or pharmaceutically acceptable salt thereof.

In a particular embodiment, the compound is

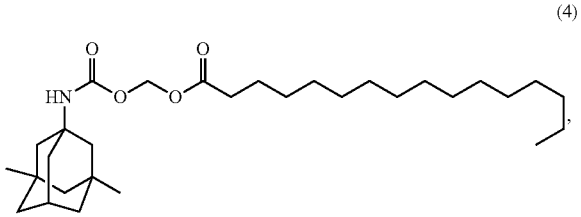 [SMILES: CCCCCCCCCCCCCCCC(=O)OCOC(=O)NC12CC3CC(C)(CC(C)(C3)C1)C2]

(4)

or a stereoisomer, mixture of stereoisomers, deuterated analog, tautomer, solvate or pharmaceutically acceptable salt thereof.

In some embodiments, provided is a compound of formula (II):

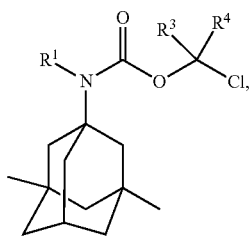

II or a stereoisomer, mixture of stereoisomers, deuterated analog, tautomer, solvate or pharmaceutically acceptable salt thereof, wherein:

$R^1$ is H, an amino-protecting group, $C_{1-6}$ alkyl, $C_{3-6}$ cycloalkyl, $C_{2-10}$ heterocyclyl, $C_{6-10}$ aryl or $C_{1-9}$ heteroaryl; and $R^3$ and $R^4$ is independently H, $C_{1-6}$ alkyl, $C_{3-6}$ cycloalkyl or $C_{6-10}$ aryl, wherein each $C_{1-6}$ alkyl, $C_{3-6}$ cycloalkyl, $C_{2-10}$ heterocyclyl, $C_{6-10}$ aryl and $C_{1-9}$ heteroaryl of $R^1$, $R^3$ and $R^4$ are each independently optionally substituted with one or more substituents selected from halo, CN, $N_3$, $NO_2$, amino, hydroxyl, mercapto, $C_{1-6}$ alkyl, $C_{1-6}$ alkylamino, $C_{1-6}$ dialkylamino, $C_{1-6}$ alkoxy, $C_{1-6}$ alkylacyl $C_{1-6}$ alkyl, $C_{2-6}$ alkenylacyl $C_{1-6}$ alkyl, $C_{1-6}$ alkylthio, $C_{1-6}$ haloalkyl, $C_{2-6}$ haloalkenyl, $C_{2-6}$ haloalkynyl, $C_{1-6}$ hydroxyalkyl, $C_{1-6}$ aminoalkyl, $C_{1-6}$ mercaptoalkyl, $C_{1-6}$ alkylamino $C_{1-6}$ alkyl, $C_{1-6}$ dialkylamino $C_{1-6}$ alkyl, $C_{1-6}$ alkoxy $C_{1-6}$ alkyl, $C_{1-6}$ alkylacyl $C_{1-6}$ alkyl, $C_{2-6}$ alkenylacyl $C_{1-6}$ alkyl, $C_{1-6}$ alkylthio $C_{1-6}$ alkyl, $C_{3-6}$ cycloalkyl, $C_{2-10}$ heterocyclyl, $C_{6-10}$ aryl and $C_{1-9}$ heteroaryl.

Process for preparing the compounds of the present disclosure as well as compositions and formulations are also provided. In one embodiment, provided a pharmaceutical composition or formulation that comprises a compound of the present disclosure and a pharmaceutically acceptable excipient or carrier. In some embodiments, the composition or formulation is a suspension. In some embodiments, the compound or the stereoisomer, the mixture of stereoisomers, the deuterated analog, the tautomer, the solvate is present in the suspension in a nanocrystalline or a microcrystalline form.

Methods for treating diseases or conditions are also provided. In some embodiments, a method for preventing, treating or ameliorating the symptoms of a neurodegenerative disease in a human in need thereof is provided. In some embodiments, a method for preventing, treating or ameliorating the symptoms of diabetes (type I or type II, without limitation) in a human in need thereof is provided. In one embodiment, the method comprises administering to the human a compound, composition or formulation of the present disclosure. The neurodegenerative disease may be one mediated by a N-methyl-D-aspartate (NMDA) receptor. Non-limiting examples of the neurodegenerative diseases include Parkinson's disease, Alzheimer's disease, Huntington's disease, atrophic myelitis, AIDS dementia, vascular dementia or the combinations thereof. In one embodiment, the human suffers from moderate to severe dementia of the Alzheimer's disease.

Additional embodiments are described throughout.

BRIEF DESCRIPTION OF THE DRAWINGS

FIG. 1 shows the in vivo pharmacokinetic profiles of various compounds after intramuscular injection into rats. Legend format: tested compound/dose (mg/kg)/converted active adamantane compound, which is memantine.

DETAILED DESCRIPTION

This disclosure provides memantine derivatives, process for making them, compositions thereof and methods of preventing, treating or ameliorating the symptoms of a neurodegenerative disease or diabetes using them.

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group.

Unless chemically or structurally required, no directionality is indicated or implied by the order in which a chemical group is written or named.

The prefix "Cu-v" indicates that the following group has from u to v carbon atoms. For example, "$C_{1-6}$ alkyl" indicates that the alkyl group has from 1 to 6 carbon atoms. It includes straight chain as well as branched chain alkyl groups.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

"Alkyl" refers to an unbranched or branched saturated hydrocarbon chain. As used herein, alkyl has 1 to 30 carbon atoms (i.e., $C_{1-30}$ alkyl), 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include, but are not limited to, methyl, ethyl, propyl, isopropyl, n-butyl, sec-butyl, isobutyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an alkyl group containing at least one carbon-carbon double bond and having from 2 to 30 carbon atoms (i.e., $C_{2-30}$ alkenyl), 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, but are not limited to, ethenyl, propenyl, butadienyl (including 1,2-butadienyl and 1,3-butadienyl).

"Alkynyl" refers to an alkyl group containing at least one carbon-carbon triple bond and having from 2 to 30 carbon atoms (i.e., $C_{2-30}$ alkynyl), 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, but are not limited to, methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include, but are not limited to, formyl, acetyl, cylcohexylcarbonyl, cyclohexylmethylcarbonyl, and benzoyl.

"Amido" refers to both a "C-amido" group which refers to the group —$C(O)NR^yR^z$ and an "N-amido" group which refers to the group —$NR^yC(O)R^z$, wherein $R^y$ and $R^z$ are independently selected from the group consisting of hydrogen, alkyl, aryl, haloalkyl, or heteroaryl; each of which may be optionally substituted.

"Amino" refers to the group —$NR^yR^z$ wherein $R^y$ and $R^z$ are independently selected from the group consisting of hydrogen, alkyl, haloalkyl, aryl, or heteroaryl; each of which may be optionally substituted.

"Amidino" refers to —$C(NH)(NH_2)$.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 14 carbon ring atoms (i.e., $C_{6-14}$ aryl), 6 to 12 carbon ring atoms (i.e., $C_{6-12}$ aryl), or 6 to 10 carbon ring atoms (i.e., $C_{6-10}$ aryl). Examples of aryl groups include, but are not limited to, phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to —$N_3$.

"Carbamoyl" refers to both an "O-carbamoyl" group which refers to the group —O—$C(O)NR^yR^z$ and an "N-carbamoyl" group which refers to the group —$NR^yC(O)OR^z$, wherein $R^y$ and $R^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include, but are not limited to, cyclopropyl, cyclobutyl, cyclopentyl, and cyclohexyl.

"Guanidino" refers to —$NHC(NH)(NH_2)$.

"Hydrazino" refers to —$NHNH_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$). "Haloalkenyl" refers to an alkenyl group as defined above, wherein one or more hydrogen atoms are replaced by a halogen. "Haloalkynyl" refers to an alkynyl group as defined above, wherein one or more hydrogen atoms are replaced by a halogen.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$,
—NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 5 to 14 ring carbon atoms (i.e., $C_{5-14}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include, but are not limited to, pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include, but are not limited to, pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety so connected at two non-adjacent atoms of the heterocyclyl with one or more (e.g. 1 or 2) four-to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one as or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Hydroxy" or "hydroxyl" refers to the group —OH.

"Oxo" refers to the group (=O) or (O).

"Nitro" refers to the group —NO$_2$.

"Sulfonyl" refers to the group —S(O)$_2$R, where R is alkyl, haloalkyl, heterocyclyl, cycloalkyl, heteroaryl, or aryl. Examples of sulfonyl include, but are not limited to, methylsulfonyl, ethylsulfonyl, phenylsulfonyl, and toluenesulfonyl.

"Alkylsulfonyl" refers to the group —S(O)$_2$R, where R is alkyl.

"Sulfonic acid" refers to the group —SO$_3$H.

"Alkylsulfinyl" refers to the group —S(O)R, where R is alkyl.

"Thiocyanate" refers to the group —SCN.

"Thiol" refers to the group —SH.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

"Amino-protecting group" refers to a grouping of atoms that, when attached to an as amino group in a molecule, masks, reduces or prevents its reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, so acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, $CH_2=CHCH_2$—, and the like, groups of the formula —C(O)R', wherein R' is, for example, methyl, phenyl, trifluoromethyl, and the like, groups of the formula —$SO_2R''$, wherein R'' is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) as including drug or substrate tissue distribution assays or in radioactive treatment of patients.

The disclosure also included compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when as administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "salt" of a given compound refers to acid addition salts and base addition salts. Acid addition salts include, for example, salts with inorganic acids and salts with organic acids. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, base addition salts can be prepared from inorganic and organic bases. Salts derived from inorganic bases include, by way of example only, sodium, potassium, lithium, ammonium, calcium and magnesium salts. Salts derived so from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like. In one embodiment, the salt can be a phosphoric acid salt.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "nanocrystalline" refers to crystals in the range of nanometers. For example, nanocrystalline compounds can be crystals with a size smaller than 100 nm.

As used herein, "microcrystalline" refers to crystals in the range of micrometers. For example, microcrystalline compounds can be crystals with a size of about 100 nm to 100 µm.

As used herein, a "suspension" is a heterogeneous mixture containing solid particles that are sufficiently large for sedimentation. The heterogeneous mixture in which the solute particles do not dissolve but get suspended throughout the bulk of the medium.

In addition, abbreviations as used herein have respective meanings as follows:

| | |
|---|---|
| d | doublet |
| DCM | dichloromethane |
| DMF | dimethylformamide |
| DMSO | dimethylsulfoxide |
| EA | ethyl acetate |
| g | gram |
| Hz | hertz |
| I.D. | internal diameter |
| i-Pr | isopropyl |
| LC-MS | liquid chrmatogrpahy-mass spectrocopy |
| m | multiplet |
| MHz | megahertz |
| MRM | multiple reaction monitoring |
| NMR | nuclear magnetic resonance |
| s | singlet |
| t | triplet |
| TLC | thin layer chromatography |

Compounds

In one embodiment, this disclosure provides a compound of formula (I):

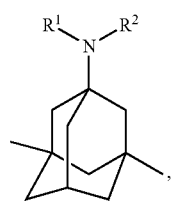

I or a stereoisomer, mixture of stereoisomers, deuterated analog, tautomer, solvate or pharmaceutically acceptable salt thereof, wherein:

$R^1$ is H, an amino-protecting group, alkyl, alkenyl, alkynyl, cycloalkyl, heterocyclyl, aryl or heteroaryl;

$R^2$ is

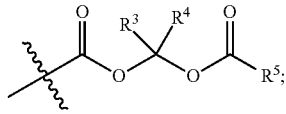

$R^3$ and $R^4$ are each independently H, alkyl, alkenyl, alkynyl, cycloalkyl or aryl; and $R^5$ is alkyl, alkenyl, alkynyl, cycloalkyl, heterocyclyl, aryl or heteroaryl, wherein each alkyl, alkenyl, alkynyl, cycloalkyl, heterocyclyl, aryl and heteroaryl of $R^1$, $R^2$, $R^3$, $R^4$, and $R^5$ are each independently optionally substituted with one or more substituents selected from halo, CN, $N_3$, $NO_2$, amino, hydroxy, mercapto, alkyl, alkylamino, dialkylamino, alkoxy, alkylacyl, alkenylacyl, alkylthio, haloalkyl, haloalkenyl, haloalkynyl, hydroxyalkyl, aminoalkyl, mercaptoalkyl, alkylaminoalkyl, dialkylaminoalkyl, alkoxyalkyl, alkylacylalkyl, alkenylacylalkyl, alkylthioalkyl, cycloalkyl, heterocyclyl, aryl and heteroaryl.

In another embodiment, this disclosure provides a compound of formula (I) as described herein, wherein $R^1$ is H, an amino-protecting group or alkyl optionally substituted with one or more substituents selected from halo, CN, $N_3$, $NO_2$, amino, hydroxyl, mercapto, alkoxy, aryl, heterocyclyl and heteroaryl.

In another embodiment, this disclosure provides a compound of formula (I) as described herein, wherein $R^3$ and $R^4$ are each independently H or alkyl.

In another embodiment, this disclosure provides a compound of formula (I) as described herein, wherein $R^5$ is alkyl, alkenyl, alkynyl, aryl or heteroaryl, wherein the alkyl, alkenyl, alkynyl, aryl, heteroaryl is optionally substituted with one or more substituents selected from halo, CN, $N_3$, NO₂, amino, hydroxyl, mercapto, alkylamino, dialkylamino, alkoxy, alkylacyl, alkenylacyl, alkylthio, aryl and heteroaryl.

In another embodiment, this disclosure provides a compound of formula (Ia):

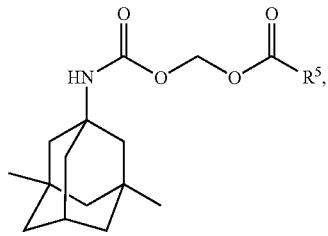

(Ia)

or a stereoisomer, mixture of stereoisomers, deuterated analog, tautomer, solvate or pharmaceutically acceptable salt thereof, wherein:

$R^5$ is alkyl, alkenyl, alkynyl, cycloalkyl, heterocyclyl, aryl or heteroaryl, wherein each alkyl, alkenyl, alkynyl, cycloalkyl, heterocyclyl, aryl and heteroaryl are each independently optionally substituted with one or more substituents selected from halo, CN, N₃, NO₂, amino, hydroxy, mercapto, alkyl, alkylamino, dialkylamino, alkoxy, alkylacyl, alkenylacyl, alkylthio, haloalkyl, haloalkenyl, haloalkynyl, hydroxyalkyl, aminoalkyl, mercaptoalkyl, alkylaminoalkyl, dialkylaminoalkyl, alkoxyalkyl, alkylacylalkyl, alkenylacylalkyl, alkylthioalkyl, cycloalkyl, heterocyclyl, aryl and heteroaryl.

In another embodiment, this disclosure provides a compound of formula (Ia) as described herein, wherein $R^5$ is alkyl, aryl or alkyl substituted with aryl. In another embodiment, $R^5$ is naphthylmethyl, phenyl, undecyl, pentadecyl, methyl, isopropyl, heptyl, tridecyl or heptadecyl.

In another embodiment, this disclosure provides a compound of formula (II):

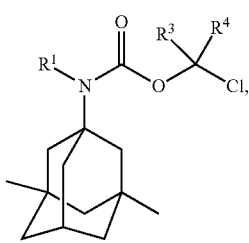

(II)

or a stereoisomer, mixture of stereoisomers, deuterated analog, tautomer, solvate or pharmaceutically acceptable salt thereof, wherein:

$R^1$ is H, an amino-protecting group, alkyl, cycloalkyl, heterocyclyl, aryl or heteroaryl; and $R^3$ and $R^4$ is independently H, alkyl, cycloalkyl or aryl, wherein each alkyl, cycloalkyl, heterocyclyl, aryl and heteroaryl of $R^1$, $R^3$ and $R^4$ are each independently optionally substituted with one or more substituents selected from halo, CN, N₃, NO₂, amino, hydroxyl, mercapto, alkyl, alkylamino, dialkylamino, alkoxy, alkylacylalkyl, alkenylacylalkyl, alkylthio, haloalkyl, haloalkenyl, haloalkynyl, hydroxyalkyl, aminoalkyl, mercaptoalkyl, alkylaminoalkyl, dialkylaminoalkyl, alkoxyalkyl, alkylacylalkyl, alkenylacylalkyl, alkylthioalkyl, cycloalkyl, heterocyclyl, aryl and heteroaryl.

In another embodiment, this disclosure provides a compound of formula (II-1):

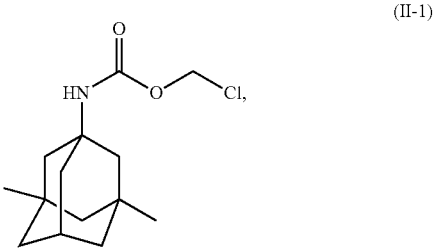 [SMILES: CC12CC3CC(C)(C1)CC(NC(=O)OCCl)(C3)C2]

(II-1)

or a stereoisomer, mixture of stereoisomers, deuterated analog, tautomer, solvate or pharmaceutically acceptable salt thereof.

In another embodiment, this disclosure provides a compound selected from:

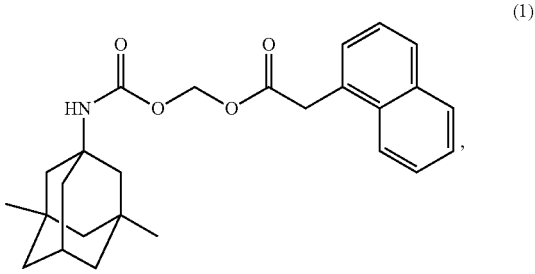

(1)

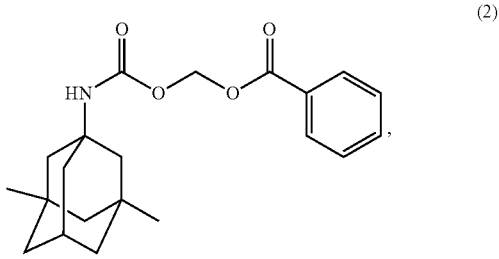

(2)

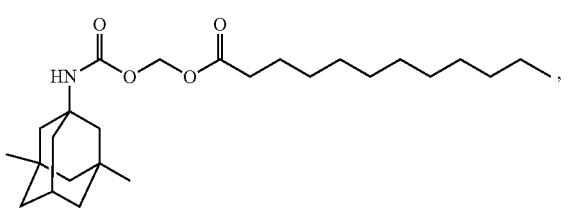

(3)

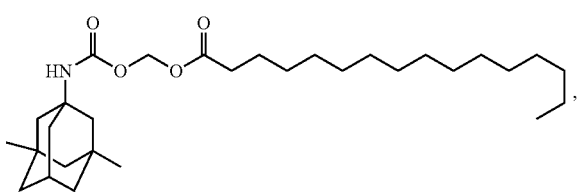

(4)

-continued (5) [structure: memantine-NH-C(=O)-O-CH2-O-C(=O)-CH3]

(6) [structure: memantine-NH-C(=O)-O-CH2-O-C(=O)-CH(CH3)2]

(7) [structure: memantine-NH-C(=O)-O-CH2-O-C(=O)-(CH2)6-CH3]

(8) [structure: memantine-NH-C(=O)-O-CH2-O-C(=O)-(CH2)12-CH3], and (9) [structure: memantine-NH-C(=O)-O-CH2-O-C(=O)-(CH2)14-CH3], or a stereoisomer, mixture of stereoisomers, deuterated analog, tautomer, solvate or pharmaceutically acceptable salt thereof.

In another embodiment, this disclosure provides a compound of formula (Ib), or a stereoisomer, a tautomer, a solvate or a pharmaceutically acceptable salt thereof, (Ib) [structure: memantine with N(R^1)(R^2)]

wherein:

$R^1$ is H, an amino-protecting group, alkyl, aryl or arylalkyl;

$R^2$ is

[structure showing: -C(=O)-O-C(R^3)(R^4)-O-C(=O)-R^5];

$R^3$ or $R^4$ is independently H, alkyl or aryl;

$R^5$ is alkyl, alkenyl, alkynyl, arylalkyl, heteroaryl, heteroarylalkyl, cycloalkyl, cycloalkylalkyl, heterocyclyl or heterocyclylalkyl;

each of the alkyl, alkenyl, alkynyl, cycloalkyl, heterocyclyl, aryl, heteroaryl, arylalkyl, heteroarylalkyl, cycloalkylalkyl, or heterocyclylalkyl is optionally substituted by one or more substituents selected from F, Cl, Br, I, CN, $N_3$, $NO_2$, amino, hydroxyl, mercapto, alkylamino, alkoxy, alkylthio, alkyl, haloalkyl, alkenyl, haloalkenyl, alkynyl, haloalkynyl, aminoalkyl, hydroxyalkyl, mercaptoalkyl, alkylaminoalkyl, alkoxyalkyl and alkylthioalkyl.

Process

As described generally, this disclosure provides in some embodiments a process of making the compounds of formula (I). In another embodiment, this disclosure provides processes for making the intermediates for the compounds of formula I as shown in the scheme below.

Scheme memantine [structure with NH2]

→

(IV) [structure with R^1NH-memantine] + [X'-C(=O)-O-C(R^3)(R^4)-X] V →

(II) [structure with R^1-N(memantine)-C(=O)-O-C(R^3)(R^4)-X] + $R^5$-C(=O)-OH III →

-continued

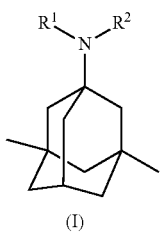

(I)

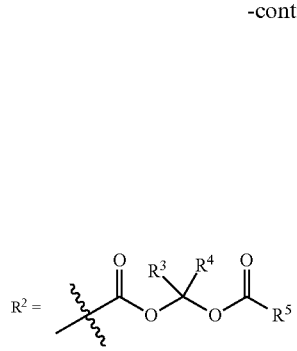

The amino group of memantine is substituted or protected to provide a compound of formula (IV), which is reacted with a compound of formula (V) in presence of a base to provide a compound of formula (II), which on reaction with a carboxylic acid of formula (III) in presence of a base and sodium iodide provides compounds of formula I as described herein.

In one embodiment, this disclosure provides a process for preparing a compound of formula (I) as described herein, comprising contacting a compound of formula (II):

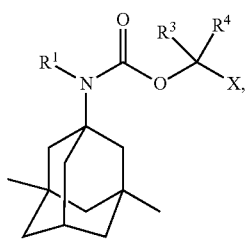

(II)

wherein X is halo, or a stereoisomer, mixture of stereoisomers, deuterated analog, or pharmaceutically acceptable salt thereof, with a compound of formula (III):

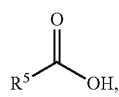

(III)

or a salt thereof, in presence of a base. In some embodiments, the process further comprises a solvent selected from N, N-dimethyl formamide, ethyl acetate, toluene, tetrahydrofuran, or a combination thereof. In some embodiments, the base is diethylamine, triethylamine, N, N-diisopropyl ethylamine, potassium carbonate, cesium carbonate, or a combination thereof. In some embodiments, the process further comprises sodium iodide.

In another embodiment, this disclosure provides a process for preparing a compound of formula (II) comprising contacting a compound of formula (IV):

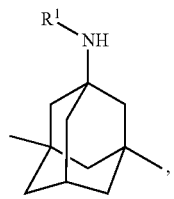

(IV)

or a stereoisomer, mixture of stereoisomers, deuterated analog, or pharmaceutically acceptable salt thereof, with a compound of formula (V):

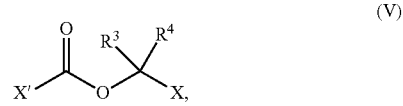

(V)

or a stereoisomer, mixture of stereoisomers, deuterated analog, or pharmaceutically acceptable salt thereof, in presence of a base, wherein X and X' are each independently halo. In some embodiments, the process further comprises a solvent selected from N, N-dimethyl formamide, ethyl acetate, toluene and tetrahydrofuran, and a combination thereof. In some embodiments, the base is diethylamine, triethylamine, N, N-diisopropyl ethylamine, potassium carbonate, cesium carbonate or a combination thereof.

Compositions and Formulations

In one embodiment, provided are compositions comprising a compound of formula (I) as described herein or a stereoisomer, mixture of stereoisomers, deuterated analog, tautomer, solvate or pharmaceutically acceptable salt thereof, and a pharmaceutically acceptable excipient or carrier. In another embodiment, the compositions are pharmaceutical compositions comprising an effective amount of a compound of formula (I) as described herein or a stereoisomer, mixture of stereoisomers, deuterated analog, tautomer, solvate or pharmaceutically acceptable salt thereof, and a pharmaceutically acceptable excipient or carrier.

In another embodiment, the compositions comprising a compound of formula (I) as described herein or a stereoisomer, mixture of stereoisomers, deuterated analog, tautomer, so solvate or pharmaceutically acceptable salt thereof, and a pharmaceutically acceptable excipient or carrier, further comprise a cholinesterase inhibitor. In another embodiment, the cholinesterase inhibitor is tacrine, donepezil, huperzine-A, galantamine, rivastigmine, or a combination thereof.

The formulations provided herein may also comprise from about 0.01% to about 90%, 0.01% to about 75%, or about 0.01% to about 50%, or about 0.01% to about 25%, or about 0.01% to about 10%, or about 0.01% to about 1% w/w of one or more emulsifying agents, wetting agents or suspending agents. Such agents include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methyl cellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium as stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract. In certain embodiments herein, the present formulations comprise polysorbate 80, microcrystalline cellulose, carboxymethylcellulose sodium and/or dextrose.

The present formulations may further comprise from about 0.01% to about 90%, or about 0.01% to about 75%, or about 0.01% to about 50%, or about 0.01% to about 25%, or about 0.01% to about 10%, or about 0.01% to about 1% of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, or other additives known in the art. Complexing agents include, but are not limited to, ethylenediaminetetraacetic acid (EDTA) or a salt thereof, such as the disodium salt, citric acid, nitrilotriacetic acid and the salts thereof.

The formulations provided herein also may comprise from about 0.01% to about 90%, or about 0.01% to about 75%, or about 0.01% to about 50%, or about 0.01% to about 25%, or about 0.01% to about 10%, or about 0.01% to about 10% of one or more solvents or co-solvents. Solvents or co-solvents for use herein include, but are not limited to, hydroxylated solvents or other pharmaceutically-acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the formulations of the present invention may comprise one or more conventional diluents known in the art. An example of a diluent is water.

In some embodiments, the compound of the present disclosure are formulated as microcrystalline or nanocrystalline suspensions. In one embodiment, the solvent of the suspension is water, saline, PBS buffer, Tween-20, Span-20 or the combination thereof. The suspension is prepared using methods known in the art and as demonstrated in Biological Example 2 by, for example, by dissolving or admixing a compound of the present disclosure with a solvent.

Therapeutic Methods and Uses

Therapeutic methods and uses for medicament manufacturing are also provided, in some embodiments. As demonstrated in the experimental examples, the compounds of the present disclosure have therapeutically favorable pharmacokinetics profiles over memantine. For instance, Biological Example 2 shows that, unlike memantine which has a half-life of about 4 hours, the half-life for Compound 4 was 101 hours, for Compound 3 was 169 hours, for Compound 1 was 357 hours, and was too high to be measurable for Compound 2. The greatly increased half-lives of these compounds is at least in part attributable to the reduced solubility of these compounds which enabled the preparation of the crystalline suspensions. Accordingly, the present data demonstrate that the compounds of the present disclosure are useful for treating diseases and conditions that are suitably treated with memantine, such as neurodegenerative and diabetic diseases and conditions.

Neurodegenerative diseases are debilitating conditions that result in progressive degeneration and/or death of nerve cells. This causes problems with movement (ataxias), or so mental functioning (dementias). Dementias are responsible for the greatest burden of disease with Alzheimer's representing approximately 60-70% of cases. In addition to Alzheimer's disease, non-limiting examples also include Parkinson's disease (PD) and PD-related disorders, prion disease, motor neurone diseases (MND), Huntington's disease (HD), spinocerebellar ataxia (SCA), spinal muscular atrophy (SMA), atrophic myelitis, AIDS dementia, and vascular dementia.

In one embodiment, this disclosure provides a method for preventing, treating or ameliorating the symptoms of a neurodegenerative disease in a human in need thereof. In one embodiment, the method entails administering to the patient an effective amount of a compound, a composition or a formulation of the present disclosure. In some embodiments, the method comprises administering to the human a compound of formula (I) as described herein, or a pharmaceutical composition of comprising a compound of formula (I) as described herein or a stereoisomer, mixture of stereoisomers, deuterated analog, tautomer, solvate or pharmaceutically acceptable salt thereof, and a pharmaceutically acceptable excipient or carrier.

In likewise embodiment, provided is the use of a compound, composition or formulation of the present disclosure for the manufacturing of a medicament for preventing, treating or ameliorating the symptoms of a neurodegenerative disease in a human in need thereof. In another embodiment, provided is a compound, composition or formulation of the present disclosure for preventing, treating or ameliorating the symptoms of a neurodegenerative disease in a human in need thereof In another embodiment, the neurodegenerative disease is mediated by a N-methyl-D-aspartate (NMDA) receptor. In another embodiment, the neurodegenerative disease is selected from the group consisting of Parkinson's disease, Alzheimer's disease, Huntington's disease, atrophic myelitis, AIDS dementia, vascular dementia or the combinations thereof. In another embodiment, the human suffers from moderate to severe dementia of the Alzheimer's disease.

In another embodiment, this disclosure provides a method for preventing, treating or ameliorating the symptoms of diabetes in a human in need thereof, wherein the method comprises administering to the human a compound of formula (I) as described herein, or a pharmaceutical composition of comprising a compound of formula (I) as described herein or a stereoisomer, mixture of stereoisomers, deuterated analog, tautomer, solvate or pharmaceutically acceptable salt thereof, and a pharmaceutically acceptable excipient or carrier. In a further embodiment, the diabetes comprises type I or type II diabetes.

In likewise embodiment, provided is the use of a compound, composition or as formulation of the present disclosure for the manufacturing of a medicament for preventing, treating or ameliorating the symptoms of diabetes in a human in need thereof. In another embodiment, provided is a compound, composition or formulation of the present disclosure for preventing, treating or ameliorating the symptoms of diabetes in a human in need thereof Methods of administering pharmaceutical compositions are well known to those of so ordinary skill in the art and include, but are not limited to, oral, microinjection, intravenous or parenteral administration. The compositions are intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the cancer being treated and the patient and the subject being treated. Single or multiple administrations can be carried out with the dose level and pattern being selected by the treating physician.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Examples related to the present invention are described below. In most cases, alternative techniques can be used. The examples are intended to be illustrative and are not limiting or restrictive to the scope of the invention. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

$^1$H Nuclear magnetic resonance (NMR) spectroscopy was carried out and the spectra were acquired in the stated solvent at around room temperature unless otherwise stated. In all cases, NMR data were consistent with the proposed structures.

Compound Preparation

Where the preparation of starting materials is not described, these are commercially available, known in the literature, or readily obtainable by those skilled in the art using standard procedures.

Example 1

Synthesis of Compound II-1

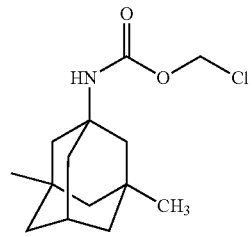

(II-1)

To a 250 mL flask, were added memantine (6.47 g, 30 mmol), triethylamine (6.66 g, 66 mmol) and 60 mL ethyl acetate. The mixture was stirred at 0° C. Then chloromethyl chloroformate (4.26 g, 33 mmol) was added dropwise, and the mixture was reacted at 0° C. so for 5 h. After the reaction was complete, water (100 mL) was added dropwise to quench the reaction, then the mixture was heated to room temperature and stirred for 30 min, the organic layer was separated and washed with saturated NaHCO$_3$ (100 mL), 0.5M HCl (100 mL) and water (100 mL). The resulted organic layer was concentrated to remove residual DCM to give a yellow oil. To the oil was added acetonitrile (12 mL) and stirred at room temperature with white solid precipitated, after stirring for 1 h. It was filtered, the filtrate was distilled to get an oil. The oil was purified by column chromatography to get colorless oil (3.8 g) in 46.7% yield.

LC-MS: M+Na: 294, M+H: 272; $^1$H NMR (400 MHz, CDCl3): δ 5.71 (s, 1H), 4.81 (s, 1H), 2.17 (s, 1H), 1.80 (s, 1H), 1.66-1.54 (m, 2H), 1.38 (d, J=12.4 Hz, 1H), 1.30 (d, J=12.3 Hz, 1H), 1.22-1.11 (m, 1H), 0.87 (s, 3H).

Example 2

Synthesis of Compound 1

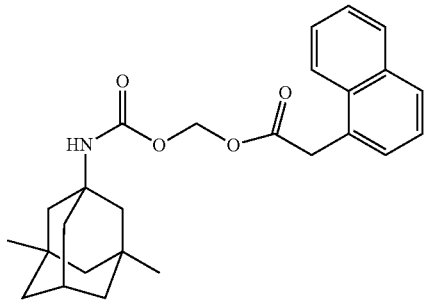

(1)

To a 100 mL flask, were added compound II-1 (2.0 g, 7.35 mmol), acetic acid (1.50 g, 8.09 mmol), triethylamine (0.89 g, 8.82 mmol), NaI (0.55 g, 3.67 mmol) and DMF (8 mL). The mixture was heated to 85° C. After reacted for 2 h, the reaction was detected by TLC. After completely reacted, the mixture was cooled to room temperature followed with addition of water (30 mL) and ethyl acetate (30 mL), then stirred for 30 min. The separated organic layer was washed with saturated NaHCO$_3$ (30 mL), 0.5M HCl (30 mL) and water (30 mL). The organic layer was separated and concentrated under reduced pressure to give a brown oil (1.1 g). The oil was purified by column chromatography to give a white solid (0.4 g) in 12.9% yield.

LC-MS: M+Na: 444; M+K: 460, 2M+Na: 865; $^1$HNMR (600 MHz, DMSO): δ 8.00-7.90 (m, 2H), 7.88 (dt, J=7.0, 3.6 Hz, 1H), 7.61-7.50 (m, 2H), 7.49-7.44 (m, 2H), 7.28 (s, 1H), 5.63 (s, 2H), 4.19 (s, 2H), 2.09 (d, J=14.5 Hz, 1H), 1.68 (s, 2H), 1.49 (q, J=12.2 Hz, 4H), 1.27 (dd, J=31.4, 11.4 Hz, 4H), 1.08 (d, J=12.2 Hz, 2H), 0.82 (s, 6H).

Example 3

Synthesis of Compound 2

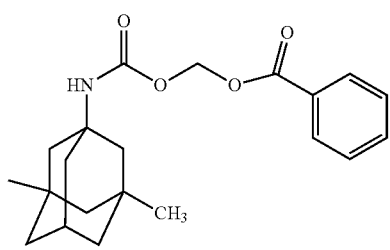

(2)

To a 100 mL flask, were added compound II-1 (2.0 g, 7.35 mmol), benzoic acid (0.98 g, 8.09 mmol), triethylamine (0.89 g, 8.82 mmol), NaI (0.55 g, 3.67 mmol) and DMF (8 mL). The mixture was heated to 85° C., after reacted for 2 h, the reaction was detected by TLC. After completely reacted, the mixture was cooled to room temperature followed with addition of water (30 mL) and ethyl acetate (30 mL), and stirred for 30 min. Then the separated organic layer was washed with saturated NaHCO$_3$ (30 mL), 0.5M HCl (30 mL) and water (30 mL). The organic layer was separated and concentrated under reduced pressure to give a brown oil (1.2 g). The oil was purified by column chromatography to give a white solid (0.7 g) in 26.6% yield.

LC-MS: M+Na: 381, 2M+Na: 737; $^1$H NMR (600 MHz, DMSO) δ 8.02-7.92 (m, 2H), 7.70 (t, J=7.4 Hz, 1H), 7.56 (t, J=7.8 Hz, 2H), 7.33 (s, 1H), 5.85 (s, 2H), 2.06 (d, J=2.5 Hz, 1H), 1.69 (s, 2H), 1.51 (q, J=11.8 Hz, 4H), 1.26 (dd, J=32.6, 11.8 Hz, 4H), 1.08 (s, 2H), 0.80 (s, 6H).

Example 4

Synthesis of Compound 5

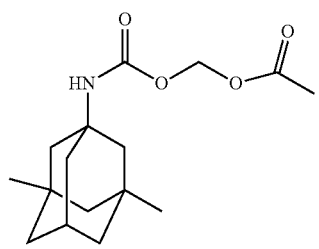

(5)

To a 100 mL flask, were added compound II-1 (3.0 g, 11.04 mmol), acetic acid (0.7 g, 11.59 mmol), triethylamine (1.34 g, 13.25 mmol), NaI (0.83 g, 5.52 mmol) and DMF (12 mL). The mixture was heated to 85° C. After reacted for 2 h, the reaction was detected by TLC. After completely reacted, the mixture was cooled to 60° C. followed with addition of water (30 mL) and ethyl acetate (30 mL), and stirred for 30 min. Then the organic layer was separated, the aqueous layer was extracted with EA (30 mL). The combined organic layer was washed with water (30 mL) twice, separated and concentrated under reduced pressure to give a brown oil (1.2 g). To the oil was added acetonitrile (15 mL), and the resulted mixture was stirred at 0° C. for 1 h with white solid precipitated. Then the mixture was filtered, the filtrate was concentrated under reduced pressure to give a yellow oil (2.0 g). The oil was purified by column chromatography to give a yellow oil (0.7 g) in 21.5% yield.

LC-MS: M+Na: 318, 2M+Na: 613; $^1$H NMR (600 MHz, DMSO) δ 7.27 (s, 1H), 5.57 (s, 2H), 2.12-1.97 (m, 4H), 1.69 (s, 2H), 1.51 (q, J=11.9 Hz, 4H), 1.29 (d, J=11.8 Hz, so 2H), 1.24 (d, J=11.8 Hz, 2H), 1.15-1.00 (m, 2H), 0.81 (s, 6H).

Example 5

Synthesis of Compound 9

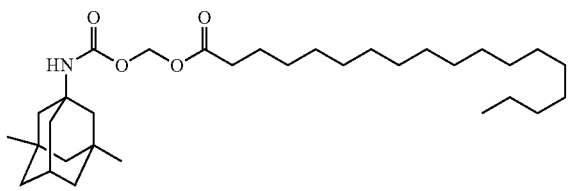

(9)

To a 100 mL flask, were added compound II-1 (3.0 g, 11.04 mmol), stearic acid (3.3 g, 11.59 mmol), triethylamine (1.34 g, 13.25 mmol), NaI (0.83 g, 5.52 mmol) and DMF (12 mL). The mixture was heated to 85° C. After reacted for 2 h, the reaction was detected by TLC. After completely reacted, the mixture was cooled to 60° C. followed with addition of water (30 mL) and toluene (30 mL), and stirred for 30 min. Then the organic layer was separated, the aqueous layer was extracted with toluene (30 mL), the combined organic layer was washed with water (30 mL) twice, separated and concentrated under reduced pressure to give a brown oil. To the oil was added acetonitrile (15 mL), the resulted mixture was stirred at room temperature for 1 h with white solid precipitated. The mixture was filtered, and the filtrate was concentrated under reduced pressure to give a yellow oil (2.2 g). The oil was purified by column chromatography to give a white solid (0.4 g) in 7% yield.

$^1$H NMR (600 MHz, DMSO) δ 7.28 (s, 1H), 5.58 (s, 2H), 2.31 (t, J=7.2 Hz, 2H), 2.10-2.05 (m, 1H), 1.69 (s, 2H), 1.50 (dd, J=20.9, 10.4 Hz, 7H), 1.33-1.14 (m, 31H), 1.09 (s, 2H), 0.86 (t, J=7.0 Hz, 3H), 0.80 (d, J=6.4 Hz, 6H).

Example 6

Synthesis of Compound 3

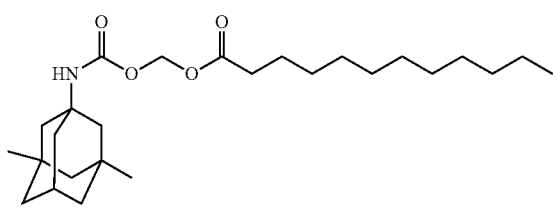

(3)

To a 100 mL flask, were added compound II-1 (2.0 g, 7.35 mmol), lauric acid (1.55 g, 8.09 mmol), triethylamine (0.89 g, 8.82 mmol), NaI (0.55 g, 3.67 mmol) and DMF (12 mL). The mixture was heated to 85° C. After reacted for 2 h, the reaction was detected by TLC. After completely reacted, the mixture was cooled to 60° C. followed with addition of water (30 mL) and toluene (30 mL), and stirred for 30 min. Then the organic layer was separated, the aqueous layer was extracted with toluene (30 mL), the combined organic layer was washed with water (30 mL) twice, the organic layer was separated and concentrated under reduced pressure to give a brown oil. To the oil was added acetonitrile (15 mL), the resulted mixture was stirred at room temperature for 1 h with white solid precipitated, then the mixture was filtered, the filtrate was concentrated under reduced pressure to give a yellow oil (1.8 g). The oil was purified by column chromatography to give a white solid (0.3 g) in 9.4% yield.

LC-MS: M+Na: 458; $^1$H NMR (600 MHz, DMSO) δ 7.26 (s, 1H), 5.57 (s, 2H), 2.31 (t, J=7.2 Hz, 2H), 2.06 (dd, J=12.1, 9.3 Hz, 1H), 1.68 (s, 2H), 1.50 (q, J=11.9 Hz, 6H), 1.33-1.15 (m, 20H), 1.08 (d, J=13.8 Hz, 2H), 0.86 (t, J=7.0 Hz, 3H), 0.80 (s, 6H).

Example 7

Synthesis of Compound 4

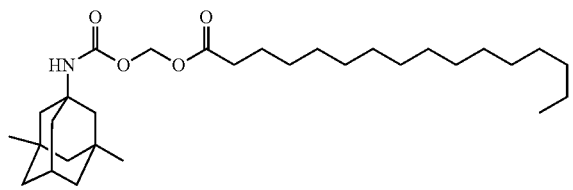

(4)

To a 100 mL flask, were added compound II-1 (2.0 g, 7.35 mmol), palmitic acid (1.98 g, 8.09 mmol), triethylamine (0.89 g, 8.82 mmol), NaI (0.55 g, 3.67 mmol) and DMF (12 mL). The mixture was heated to 85° C. After reacted for 2 h, the reaction was detected by TLC. After completely reacted, the mixture was cooled to 60° C. followed with addition of water (30 mL) and toluene (30 mL), and stirred for 30 min. Then the organic layer was separated, the aqueous layer was extracted with toluene (30 mL), the combined organic layer was washed with water (30 mL) twice, the organic layer was separated and concentrated under reduced pressure to give a brown oil. To the oil was added acetonitrile (15 mL), the mixture was stirred at room temperature for 1 h with white solid precipitated, the mixture was filtered, and the filtrate was concentrated under reduced pressure to give a yellow oil (1.1 g). The oil was purified by column chromatography to give a white solid (0.2 g) in 5.5% yield.

$^1$H NMR (600 MHz, DMSO) δ 7.28 (s, 1H), 5.58 (s, 2H), 2.31 (t, J=7.2 Hz, 2H), 2.10-2.02 (m, 1H), 1.69 (s, 2H), 1.58-1.41 (m, 7H), 1.26 (d, J=21.8 Hz, 27H), 1.08 (d, J=12.8 Hz, 2H), 0.86 (t, J=7.0 Hz, 3H), 0.80 (d, J=6.4 Hz, 6H).

Example 8

Synthesis of Compound 7

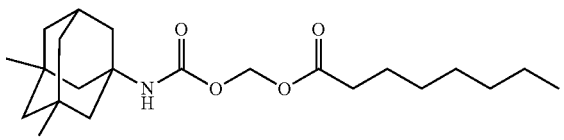

(7)

To a 100 mL flask, were added compound II-1 (7.5 g, 27.5 mmol), octanoic acid (7.92 g, 55 mmol), triethylamine (2.07 g, 13.8 mmol), NaI (3.06 g, 30.25 mmol) and EA (75 mL). The mixture was heated to 60° C. After reacted for 24 h, the reaction was detected by TLC. After completely reacted, the mixture was cooled to 30° C. and filtered, the filtrate was washed with saturated $K_2CO_3$ and water, separated organic layer was concentrated at 40° C. for 1 h to give a yellow oil (6 g) in 58% yield, crude product was purified by column so chromatography to give an oil (2.6 g) in 40% yield.

LC-MS: M+Na: 402; $^1$H NMR (400 MHz, DMSO) δ 7.26 (s, 1H), 5.58 (s, 2H), 2.32 (t, J=7.2 Hz, 2H), 2.07 (s, 1H), 1.69 (s, 2H), 1.51 (s, 6H), 1.25 (s, 12H), 1.09 (s, 2H), 0.86 (s, 3H), 0.81 (s, 6H).

Example 9

Synthesis of Compound 8

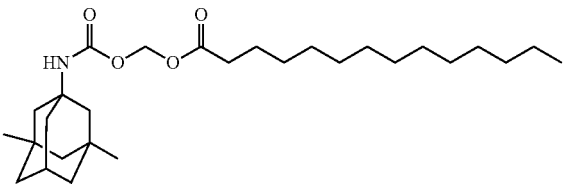

(8)

To a 100 mL flask, were added compound II-1 (15 g, 55 mmol), tetradecanoic acid (25.1 g, 110 mmol), triethylamine (6.1 g, 60.5 mmol), NaI (4.13 g, 27.5 mmol) and EA (150 mL). The mixture was heated to 60° C., after 24 h, the reaction was detected by TLC. After completely reacted, the mixture was cooled to 30° C. and filtered, filtrate was concentrated under reduced pressure to give a yellow oil. To the oil was added acetonitrile (200 mL), it was stirred at 10° C. for 1 h and filtered, filtrate was concentrated at 40° C. for 1 h to give a yellow oil (16 g). The crude product was purified by column chromatography to give a white sticky substance (8 g) in 50% yield.

$^1$H NMR (400 MHz, DMSO) δ 7.26 (s, 1H), 5.58 (s, 2H), 2.31 (t, J=7.2 Hz, 2H), 2.07 (s, 1H), 1.69 (s, 2H), 1.51 (t, J=8.3 Hz, 6H), 1.33-1.19 (m, 24H), 1.09 (s, 2H), 0.89-0.78 (m, 9H).

Example 10

Synthesis of Compound 6

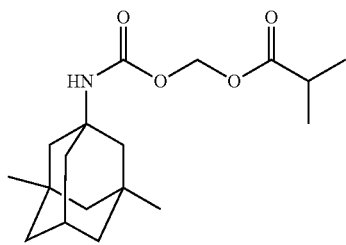

(6)

To a 100 mL flask, were added compound II-1 (3.6 g, 13.3 mmol), isobutyric acid (1.76 g, 110 mmol), DIPEA (2.58 g, 20 mmol), NaI (0.4 g, 2.66 mmol) and EA (36 mL). The mixture was heated to 70° C., after 18 h, the reaction was detected by TLC. After completely reacted, the mixture was cooled to 25° C. followed by addition of water (36 mL), stirred for 30 min, separated organic layer was washed with saturated NaHCO$_3$, the organic layer was separated and concentrated under reduced pressure at 50° C. to give a yellow solid (3.9 g) in 90.9% yield. The crude product was dissolved in ethanol and the solution was stirred at 25° C. with 0.5V water added slowly, stirred for 30 min. The mixture formed a suspension, it was filtered, filter cake was dried at 50° C. under reduced pressure for 16 h to give a white solid (1.75 g) in 44.9% yield.

LC-MS: M+Na: 346; $^1$H NMR (400 MHz, DMSO) δ 7.27 (s, 1H), 5.59 (s, 2H), 2.57 (d, J=7.0 Hz, 1H), 2.08 (s, 1H), 1.69 (s, 2H), 1.51 (s, 4H), 1.33-1.21 (m, 4H), 1.08 (d, J=7.0 Hz, 8H), 0.81 (s, 6H).

BIOLOGICAL EXPERIMENTS

Biological Example 1. Stability in Microsomes of Human Liver Cells

This example examines the conversion of various compounds of the present disclosure to active adamantane compound, which is memantine, in microsomes of human liver cells and demonstrates that the compounds of the present disclosure maintain a slow conversion rate and high stability under these conditions.

Materials and Methods

Analytical LC/MS/MS systems: Agilent 1200 Series vacuum degasser, dual-injection pump, orifice autosampler, column incubator, charged spray ionization (ESI) source, and Agilent G6430 three-stage quadrupole mass spectrometer. The quantitative analysis is performed in the MRM mode, with the following MRM conversion parameters:

| | |
|---|---|
| Multi-reaction detection scan | 180.2→163.1 |
| Fragmentation voltage | 15 V |
| Capillary voltage | 3500 V |
| Dryer temperature | 350° C. |
| Atomizer | 40 psi |
| Dryer flow rate | 9 L/min |

Analytical Agilent Poroshell HPH-C18: 2.1×50 mm, 2.7 μM column, 20 μL of sample was injected. Conditions: mobile phase with ammonium formate+0.1% formic acid (A) and methanol+2 mM ammonium formate+0.1% formic acid (B). The flow rate was 0.3 mL/min. The mobile phase gradient is as follows:

| Time | Mobile Phase B Gradient |
|---|---|
| 0.3 min | 10% |
| 1.2 min | 75% |
| 1.8 min | 90% |
| 2.8 min | 95% |
| 2.9 min | 10% |
| 4.0 min | stop |

Agilent 6330 Series LC/MS/MS spectrometer was equipped with G1312A binary injection pump, G1367A automatic sampler and MS/MS detector; LC/MS/MS was used with ESI source. Suitable cationic model treatments and MRM conversion were used for each analyte using standard solution for optimal analysis. The Agilent Poroshell HPH-C18 column was used during the analysis with a specification of 100×4.6 mm I.D., 5 μM. The mobile phase included ammonium formate+0.1% formic acid (A) and methanol+2 mM ammonium formate+0.1% formic acid (B). The flow rate was 0.3 mL/min; the column temperature was maintained at 40° C.; 20 μL of sample was injected.

A human liver microsomal incubation system was used for the testing. The incubation mixtures included human or rat liver microsomes (0.5 mg protein/mL), the tested compound was provided at 1 μM. The compound was dissolved in DMSO and diluted with acetonitrile water and mixed with a mixture of liver microparticle potassium phosphate buffer solution (pH=7.4). The above operations were done on wet ice, and incubated in a thermostatic incubator at 37° C. At different time points (0, 60 and 120 min), ice-cold acetonitrile was added to terminate the reaction. NADPH was not added during the reaction, and the effect of esterase on its conversion was examined. Samples were stored at −80° C. until LC/MS/MS analysis was performed.

The conversion of the compounds of the disclosure to active adamantane compound, which is memantine in the human liver microsome was determined by LC/MS/MS.

Results

Table 1 shows the results of stability testing of certain compounds as prepared in the above examples. The compounds tested were converted, in the microsomes of human liver cells, to active adamantane compound, which is memantine, at fairly slow rates. Memantine (MJG) was used as control. These tested compounds are quite stable under these conditions.

TABLE 1

Stability of tested compounds in microsomes of human liver cells.

| Incubation time (min) | Percentage of Remaining or Converted Active Adamantane Compound | | | | |
|---|---|---|---|---|---|
| | MJG | Compound 1 | Compound 2 | Compound 3 | Compound 4 |
| 0 (4° C.) | 100 | 9 | 16 | 0.7 | 0.4 |
| 0 (37° C.) | 90 | 14 | 67 | 3.3 | 2 |
| 60 (37° C.) | 98 | 108 | 134 | 35.6 | 25.3 |
| 120 (37° C.) | 98 | 101 | 118 | 35.6 | 34 |

Biological Example 2. In Vivo Pharmacokinetics Testing

This example describes an in vivo testing for pharmacokinetics of various compounds of the present disclosure and demonstrate their slow and stable conversion to active adamantane compound, which is memantine.

Materials and Methods

Analytical LC/MS/MS systems: Agilent 1200 Series vacuum degasser, dual-injection pump, orifice autosampler, column incubator, charged spray ionization (ESI) source, and Agilent G6430 three-stage quadrupole mass spectrometer. The quantitative analysis is performed in the MRM mode, with the following MRM conversion parameters:

| | |
|---|---|
| Multi-reaction detection scan | 180.2→163.1 |
| Fragmentation voltage | 15 V |
| Capillary voltage | 3500 V |
| Dryer temperature | 350° C. |
| Atomizer | 40 psi |
| Dryer flow rate | 9 L/min |

Waters XBridge TMC18, 2.1×30 mm, 3.5 µM column; 20 µL of sample was injected in each run. Conditions: The mobile phase included ammonium formate+2 mM ammonium formate+0.1% formic acid (A) and methanol+2 mM ammonium formate+0.1% formic acid (B). The flow rate was 0.35 mL/min. The mobile phase gradient is as follows:

| Time | Mobile Phase B Gradient |
|---|---|
| 0.8 min | 10% |
| 1.4 min | 75% |
| 2.6 min | 95% |
| 2.7 min | 10% |
| 3.5 min | stop |

Additional instruments and reagents included Agilent 6330 Series LC/MS/MS spectrometer equipped with a G1312A Binary Injection Pump, G1367A autosampler and MS/MS Detector for analysis; LC/MS/MS spectrometer with ESI source. Suitable cationic model treatments and MRM conversion were used for each analyte using standard solution for optimal analysis. Waters XBridge TMC18 was used with specifications of 2.1×30 mm, 3.5 µM. The reaction was carried out with ammonium formate+2 mM ammonium formate+0.1% formic acid (A) and methanol+2 mM ammonium formate+0.1% formic acid (B). The flow rate was 0.35 mL/min; the column temperature was maintained at 40° C.; 10 µL of sample was injected.

Results

This example conducted pharmacokinetic studies of various compounds of the present disclosure in rats. The compounds were subjected to pretreatment including grinding and sieving, and were then added to a mixture formed by dissolving and dispersing in Tween-20 and/or Span-20. The mixtures were uniformly dispersed and fixed. The suspensions were pulverized by a ball mill after administration. Memantine (MJG, 17.5 mg/kg) or tested compounds (75 or 37.5 mg/kg) were administered by intramuscular administration. Whole blood was collected at 0.25, 1, 2, 5, 7, 24, 48, 72, 96, 120, 148 and 196 h, was centrifuged at 12,000 g for 2 minutes. Plasma was collected and stored at −20° C. or −70° C. until the LC/MS/MS analysis was performed.

Table 2 provides the pharmacokinetics (PK) data of the compounds in rats. The compounds exhibited excellent pharmacokinetic properties and sustained release profiles with respect to peak time (Tmax), half-life ($T_{1/2}$) and exposure (AUClast). The absorption and release curves were more flat than the control (memantine in solution). The Tmax was between 2-180 h. At 196 h, memantine concentrations were maintained at about 3 ng/mL or higher.

TABLE 2

In vivo Pharmacokinetics Properties of the Compounds

| Sample | Formulation | Dose (mg/kg) | AUClast (h*ng/ml) | Cmax (ng/ml) | T½ (h) | Tmax (h) |
|---|---|---|---|---|---|---|
| MJG | solution | 17.5 | 11767 | 1945 | 4 | 1.33 |
| Compound 1 | suspension | 75 | 3860 | 33.57 | 357 | 24 |
| Compound 2 | suspension | 75 | 4718 | 38.2 | N/A* | 180 |
| Compound 3 | suspension | 75 | 9910 | 519.3 | 169 | 2 |
| Compound 4 | suspension | 37.5 | 1227 | 30.87 | 101 | 5.67 |

*N/A: not obtained due to flat concentration curve

The memantine derivatives disclosed herein, in suspensions, showed reduced solubility as compared to memantine (in solution), and exhibited favorable slower release profiles in vivo. These examples therefore demonstrate that the compounds of the present disclosure provide slow and consistent release of active adamantane compound, which is memantine, and thereby are useful in treating diseases with improved efficacy and reduced adverse effects than memantine.

The methods and variances described herein as representative of preferred embodiments are exemplary and are not intended as limitations on the scope of the disclosure. Thus, additional embodiments are within the scope of the disclosure and within the following claims.

What is claimed is:

1. A compound of formula (I):

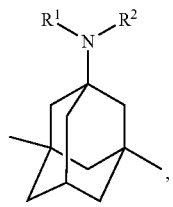

or a stereoisomer, deuterated analog, tautomer, solvate or pharmaceutically acceptable salt thereof, wherein:

$R^1$ is H, an amino-protecting group, alkyl, alkenyl, alkynyl, cycloalkyl, heterocyclyl, aryl or heteroaryl;

$R^2$ is

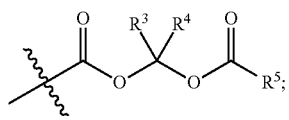

$R^3$ and $R^4$ are each independently H, alkenyl, alkynyl, cycloalkyl or aryl; and $R^5$ is alkyl, alkenyl, alkynyl, cycloalkyl, heterocyclyl, aryl or heteroaryl, wherein each alkyl, alkenyl, alkynyl, cycloalkyl, heterocyclyl, aryl and heteroaryl of $R^1$, $R^2$, $R^3$, $R^4$, and $R^5$ are each independently optionally substituted with one or more substituents selected from halo, CN, $N_3$, $NO_2$, amino, hydroxy, mercapto, alkyl, alkylamino, dialkylamino, alkoxy, alkylacyl, alkenylacyl, alkylthio, haloalkyl, haloalkenyl, haloalkynyl, hydroxyalkyl, aminoalkyl, mercaptoalkyl, alkylaminoalkyl, dialkylaminoalkyl, alkoxyalkyl, alkylacylalkyl, alkenylacylalkyl, alkylthioalkyl, cycloalkyl, heterocyclyl, aryl and heteroaryl.

2. The compound of claim 1, wherein $R^1$ is H, an amino-protecting group or $C_{1-6}$ alkyl optionally substituted with one or more substituents selected from halo, CN, $N_3$, $NO_2$, amino, hydroxyl, mercapto, $C_{1-6}$ alkoxy, $C_{6-10}$ aryl, $C_{2-10}$ heterocyclyl and $C_{1-9}$ heteroaryl.

3. The compound of claim 1, wherein $R^3$ and $R^4$ are each H.

4. The compound of claim 1, wherein $R^5$ is $C_{1-30}$ alkyl, $C_{2-30}$ alkenyl, $C_{2-30}$ alkynyl, $C_{6-14}$ aryl or $C_{1-9}$ heteroaryl, wherein the $C_{1-30}$ alkyl, $C_{2-30}$ alkenyl, $C_{2-30}$ alkynyl, $C_{6-14}$ aryl, or $C_{1-9}$ heteroaryl is optionally substituted with one or more substituents selected from halo, CN, $N_3$, $NO_2$, amino, hydroxyl, mercapto, $C_{1-30}$ alkylamino, $C_{1-30}$ dialkylamino, $C_{1-30}$ alkoxy, $C_{1-30}$ alkylacyl, $C_{2-30}$ alkenylacyl, $C_{1-30}$ alkylthio, $C_{6-14}$ aryl and $C_{1-9}$ heteroaryl.

5. The compound of claim 4, wherein $R^5$ is naphthylmethyl, phenyl, benzyl, methyl, propyl, isopropyl, octyl, hendecyl, tridecyl, pentadecyl or heptadecyl.

6. The compound of claim 1 represented by formula (Ia):

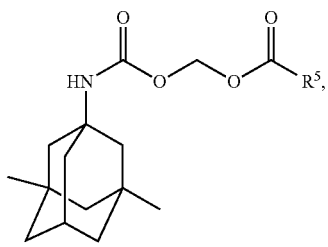

or a stereoisomer, deuterated analog, tautomer, solvate or pharmaceutically acceptable salt thereof, wherein:

$R^5$ is $C_{1-30}$ alkyl, $C_{6-10}$ aryl or $C_{1-30}$ alkyl substituted with $C_{6-10}$ aryl.

7. A compound selected from the group consisting of:

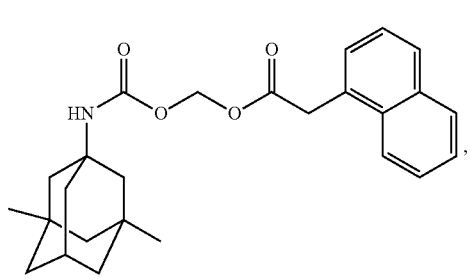

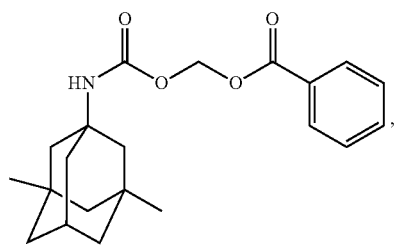

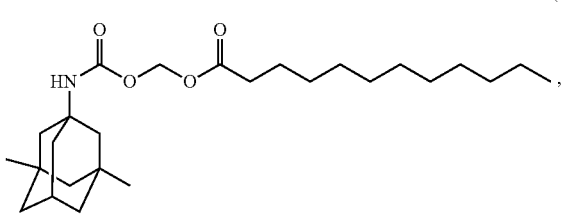

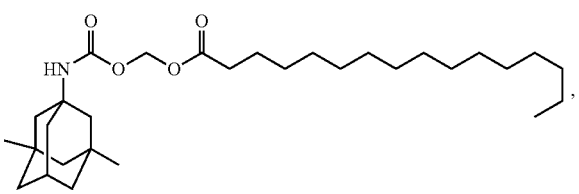

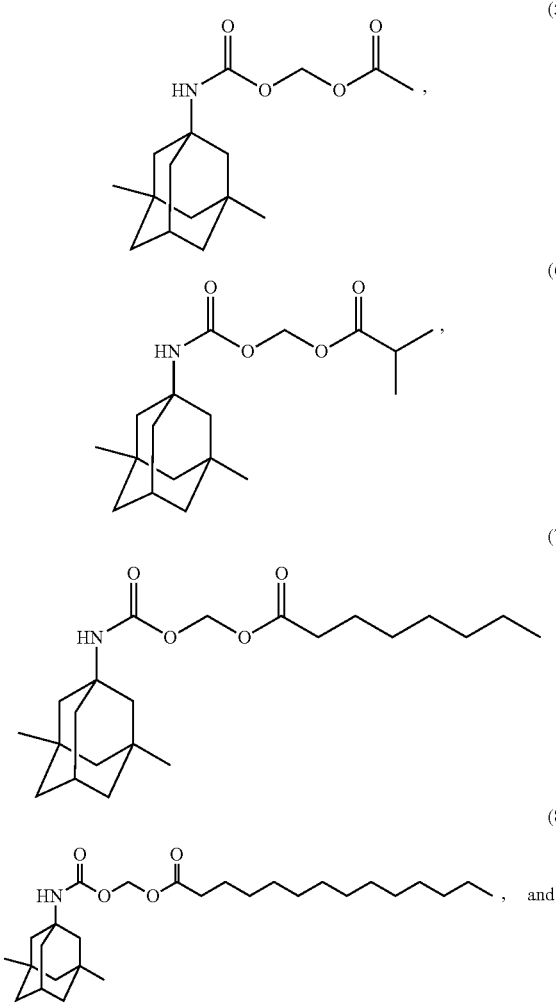
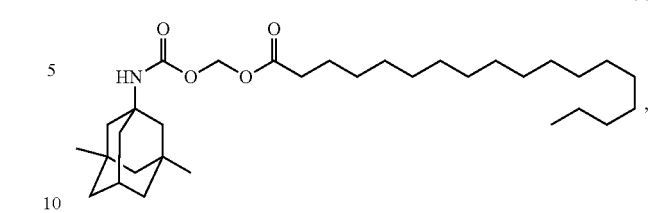

or a stereoisomer, deuterated analog, tautomer, solvate or pharmaceutically acceptable salt thereof.

8. A pharmaceutical composition comprising a compound of claim 1 or a stereoisomer, deuterated analog, tautomer, solvate or pharmaceutically acceptable salt thereof, and a pharmaceutically acceptable excipient or carrier.

9. The pharmaceutical composition of claim 8, further comprising a cholinesterase inhibitor.

10. The pharmaceutical composition of claim 9, wherein the cholinesterase inhibitor is tacrine, donepezil, huperzine-A, galantamine, rivastigmine, or a combination thereof.

11. The pharmaceutical composition of claim 8, which is a suspension.

12. The pharmaceutical composition of claim 11, wherein the compound or the stereoisomer, the deuterated analog, the tautomer, or the solvate is present in the suspension in a nanocrystalline or a microcrystalline form.

13. A method for treating Alzheimer's disease in a human in need thereof, wherein the method comprises administering to the human a compound of claim 1.

14. A method for inhibiting the activity of N-methyl-D-aspartate (NMDA) receptor in a human in need thereof, wherein the method comprises administering to the human a compound of claim 1.

15. A method for treating or ameliorating the symptoms of diabetes in a human in need thereof, wherein the method comprises administering to the human a compound of claim 1.

* * * * *